United States Patent [19]

DiGiacomo et al.

[11] 4,235,991
[45] Nov. 25, 1980

[54] LAYERED SULFONATE END TERMINATED ORGANOPHOSPHORUS INORGANIC POLYMERS

[75] Inventors: Peter M. DiGiacomo, Mission Viego; Martin B. Dines, Santa Ana, both of Calif.

[73] Assignee: Occidental Research Corporation, Irvine, Calif.

[21] Appl. No.: 966,197

[22] Filed: Dec. 4, 1978

[51] Int. Cl.$^2$ .................... C08F 130/02; C07F 7/00
[52] U.S. Cl. ................... 528/391; 260/429.3; 528/395
[58] Field of Search ............ 260/429.3, 429.5, 435 R, 260/429.1, 429.2, 429 R; 528/391, 395

[56] References Cited

U.S. PATENT DOCUMENTS

| | | | |
|---|---|---|---|
| 2,841,611 | 7/1958 | Bersworth | 260/435 R X |
| 2,879,283 | 3/1959 | Gaertner et al. | 260/435 R X |
| 2,917,528 | 12/1959 | Ramsey et al. | 260/435 R X |
| 3,052,653 | 9/1962 | Iannicelli | 260/435 R X |
| 3,055,925 | 9/1962 | Hartle | 260/429 R X |
| 3,177,233 | 4/1965 | Calhoun | 260/429 R X |
| 3,926,821 | 12/1975 | LeSuer | 260/429 R X |
| 3,940,436 | 2/1976 | Kerst | 260/435 R X |
| 3,957,858 | 5/1976 | Kerst | 260/429 R X |

OTHER PUBLICATIONS

Chemical Abstracts, 80 122698f (1974).
Alberti et al., J. Inorg. Nucl. Chem., 40, pp. 1113–1117 (1978).

*Primary Examiner*—Helen M. S. Sneed
*Attorney, Agent, or Firm*—Christie, Parker & Hale

[57] ABSTRACT

Sulfo-organophosphonic acid compounds react by a metathesis reaction in a liquid medium with tetravalent metal ions, yielding layered crystalline to amorphous inorganic polymers having the empirical formula $M(O_3PRSO_3H)_2$ where M is a tetravalent metal and R is an organic group covalently bonded to phosphorus and the terminal sulfonic acid group. One use for the compounds is as ion exchangers.

9 Claims, 10 Drawing Figures

- DEIONIZED WATER
- × SATURATED SALT SOLUTION
- ▲ PRE-DISPERSED SOLID

LAYERED SULFONATE END TERMINATED ORGANOPHOSPHORUS INORGANIC POLYMERS

CROSS REFERENCE TO RELATED APPLICATIONS

This application is related to our application Ser. No. 945,971, filed Sept. 26, 1978 and titled "Process for Preparing Layered Organophosphorus Inorganic Polymers," and our application Ser. No. 952,228, filed on Oct. 17, 1978 and titled "Layered Carboxy End Terminated Organophosphorus Inorganic Polymers," the entire disclosures of which are incorporated herein by this reference.

BACKGROUND OF THE INVENTION

The present invention is directed to solid inorganic polymers having sulfonic acid groups anchored to the surfaces of the polymers. The polymers formed can be layered crystals which display intercalation activity, or they can be partially or totally amorphous.

The interface surfaces of solids are responsive regions of chemical and physical action. Many practical chemical and physical phenomena such as absorption, corrosion, inhibition, heterogeneous catalysis, lubrication, ion exchange activity, adhesion and wetting and electrochemical activity occur on or as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in the active sites which arises from the nature of their surface structure. Furthermore, much of the active sites are usually buried within the surface, and as a result of these two factors, elevated temperature and low conversions are typically required to make a process effective. Exceptions in which honogeneous agents have been used include the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Many inorganic solids crystallize with a layered structure and present sites for anchoring active groups. In this form, sheets or slabs with a thickness of from one to more than seven atomic diameters lie upon one another. With references to FIG. 1, strong ionic or covalant bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "intercalation," the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, the potential surface is greater than the actual surface by a factor of the number of lamella composing the crystal. This value is typically on the order of $10^2$–$10^4$. Although edge surface is practically insignificant compared to basal surface, it is critical to the rate of intercalation, since the inclusion process always occurs via the edges. This is because bonding within the sheets is strong, and therefore, penetration of the sheets is an unlikely route into the crystal.

Previous studies of the intercalative behavior of layered compounds have mainly been conducted by solid state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective fixation or catalytic conversion, specific groups must be present which effect such activity. There might also be some preferable geometric environment about each site, as well as some optimal site-to-site spacing. These considerations have not been extensively applied to intercalation chemistry simply because such kinds of active groups required are not found on layered surfaces.

A approach in which catalytically active agents have been intercalated into graphite or clays for subsequent conversions has been described in "Advanced Materials in Catalysis," Boersma, Academic Press, N.Y. (1977), Burton et al., editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

One of the few layered compounds which have available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accomodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be a promising inorganic cation exchanger for alkali, ammonium and actinide ions, see Alberti, "Accounts of Chemistry Res." 11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. A. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

A very recently reported effort in the field is Alberti, et al, "J. Inorg. Nucl. Chem.," 40, 1113 (1978) which is incorporated herein by reference. A method similar to that of this invention for the preparation of zorconium bis (benzenephosphonate), zirconium bis (hydroxymethanephosphonate) monohydrate, and zirconium bis (monoethylphosphate) is described, with descriptions of the properties for these products.

SUMMARY OF INVENTION

According to the present invention there is provided inorganic polymers having sulfonic acid groups pendant to phosphorus atoms wherein the phosphorus atoms are, in turn, linked by oxygen to tetravalent metal atoms. The pendant sulfonic acid groups are coupled to phosphorus directly or through an organic group.

Compounds provided in accordance with the invention are inorganic polymers providing pendant sulfonic acid groups and which include units of the formula:

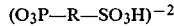

wherein R is an organo group in which the phosphorus is structurally linked through each of the available oxygens to a tetravalent metal selected from the group consisting of zirconium, cerium, thorium, uranium, hafnium, lead, titanium, and mixtures thereof and wherein the molar ratio of phosphorus to tetravalent metal in said inorganic polymer is about 2 to 1.

Sulfonic acid homopolymers which are inorganic phosphonate polymers have the empirical formula:

wherein R is as defined above and M is a tetravalent metal.

The compounds of the invention are formed by a liquid media reaction in which at least one sulfonic phosphorus-acid compound of the formula:

wherein R is as defined above, is reacted with at least one tetravalent metal ion selected from the group consisting of zirconium, cerium, thorium, uranium, lead, hafnium, titanium and mixtures thereof. The molar ratio of phosphorus to the tetravalent metal in the product is 2 to 1. Reaction, however, preferably occurs in the presence of an excess of phosphorus containing acid reactants to consume all of the metal ions and the metal ion is provided as a compound soluble in the liquid media.

The sulfonic acid intermediates can be prepared through derivatives such as acid halides, amides or esters. Such intermediates provide convenience in non-aqueous based syntheses. Conversion to the sulfonic acid may be carried out before or after formation of the organophosphorus inorganic polymer, resulting in different degrees of crystallinity.

Other organophosphorus acid compounds may be present for reaction to form part of the inorganic polymer which is the product of the reaction. These organophosphorus acid compounds need not contain sulfonic acid functions. They may contain substituents which have functional groups that interact with the sulfonate groups in the product. Donor functional groups such as nitrile, ether, ester, amide, oxo, carboxy, hydroxy, sulfide, hydrosulfide and the like influence the ion exchange selectivity and the acidity of nearby sulfonate groups. These substituents may also contain ionic groups thereby rendering the products ampholytic salt exchangers. Phosphoric and/or phosphorous acid can also be present as reactive dilutants.

The products formed are layered crystalline to semi-crystalline to amorphous in nature. The pendant sulfonic acid groups serve as ion exchangers, as intermediates for the addition or substitution of other functional groups, and as catalysts for esterification reactions or alcohol dehydration.

Multicomponent polymers, containing other organic groups interspersed with the sulfonate group, can be prepared. In addition, a mixture of two or more sulfonic acids can be used in the preparation, e.g., one acyclic and one cyclic acid.

THE DRAWINGS

Figure 1:
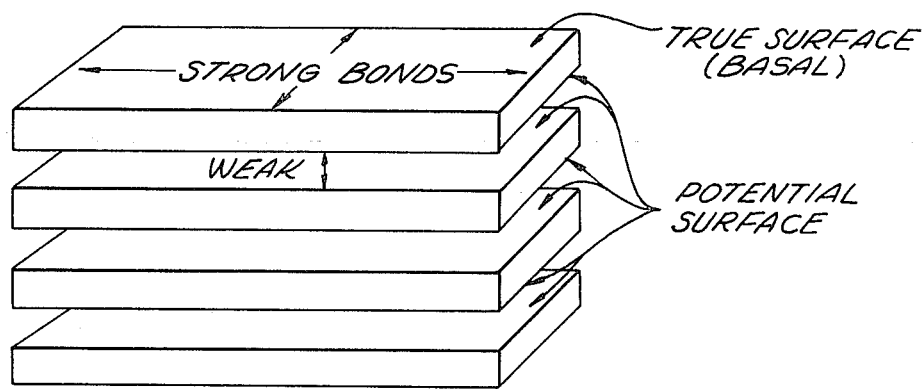
FIG. 1 illustrates a layered microcrystal. Each lamellar slab is formed of strong covalent bonds and has a thickness of about 10 atoms.
Figure 2:
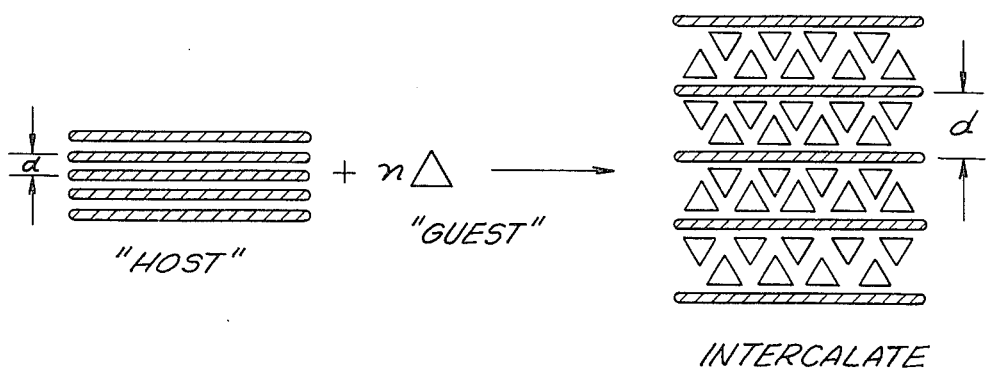
FIG. 2 illustrates intercalation where the interlayer distance is shown as "d."
Figure 3:
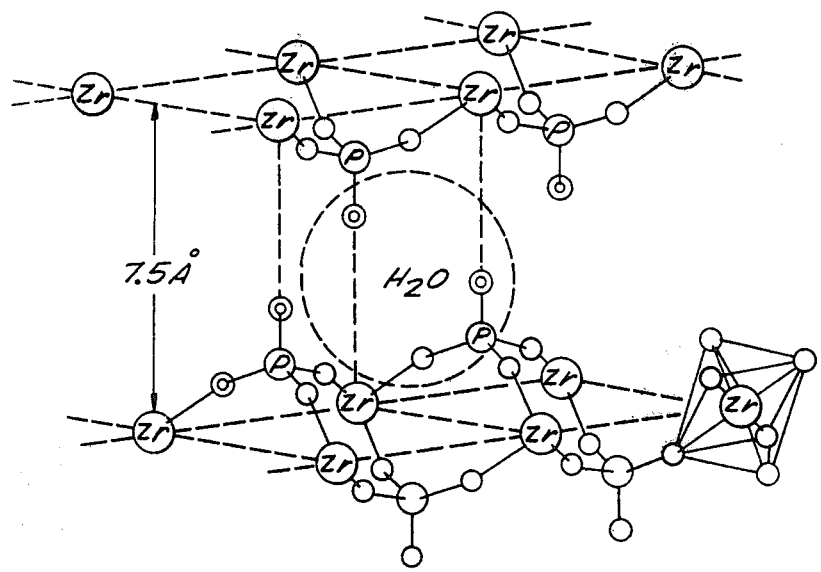

FIG. 3 illustrates the accepted structure for zirconium phosphate and spacing between layers. The dashed lines between zirconium (Zr) atoms is to establish the plane between them. In the drawing P=Phosphorus, O=Oxygen and water of hydration as shown.

Figure 4:
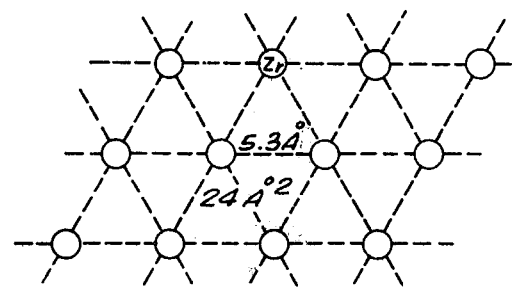

FIG. 4 illustrates a projection of zirconium plane showing accepted spacing between Zr atoms and the available linkage area.

Figure 5:
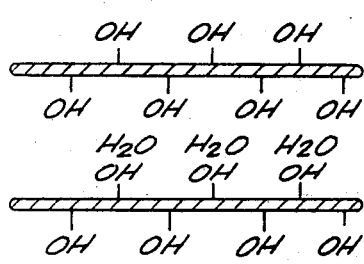

FIG. 5 is a symbolized depiction of spaced zirconium phosphate layers showing covalently bonded hydroxyl groups and water of hydration.

Figure 6:
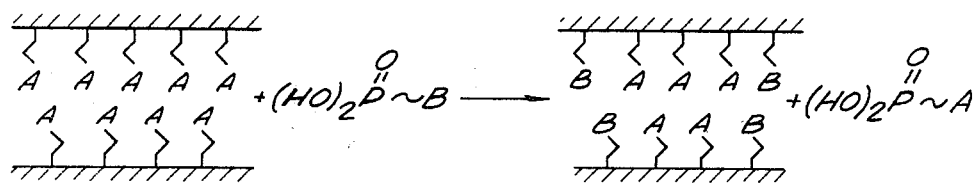

FIG. 6 illustrates an exchange reaction where anchored SO₃H groups ("A") are to be substituted by "B," and represents the portion of the organo group linking the terminal group "A" or "B" to the crystals or the organophosphorus acid compound reactant.

Figure 7:
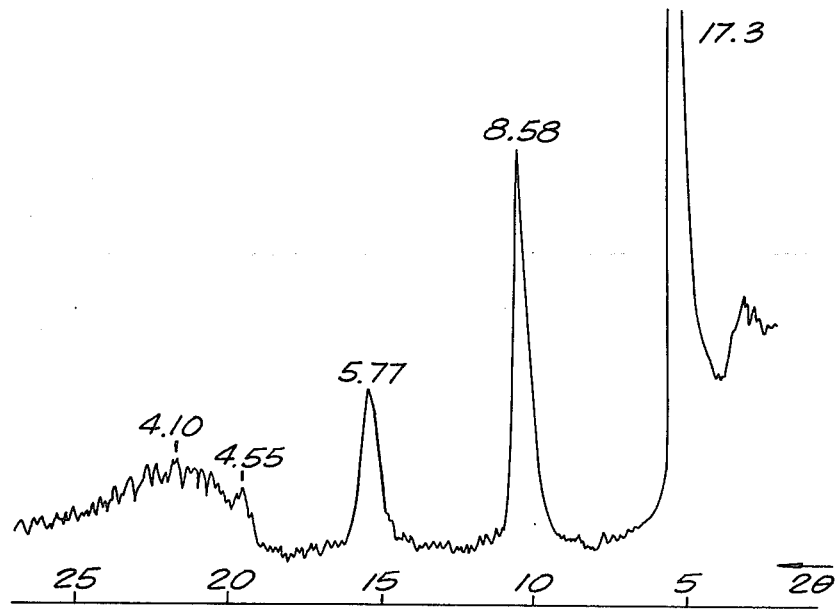

FIG. 7 is an X-ray powder diffraction pattern for semi-crystalline zirconium 3-sulfopropyl phosphonate as prepared in Example 2.

Figure 8:
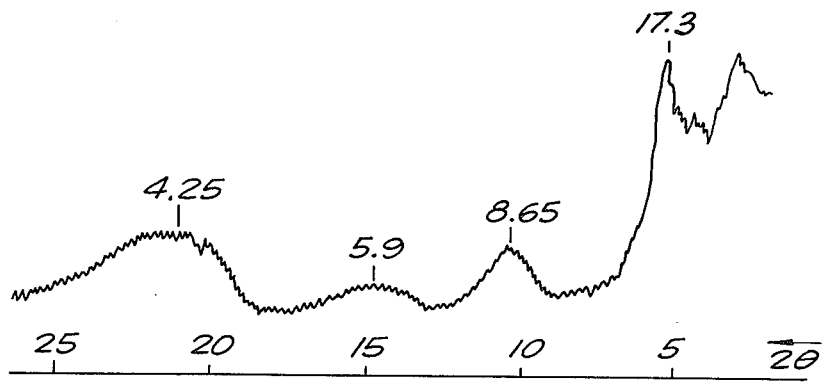

FIG. 8 is an X-ray powder diffraction pattern for highly crystalline zirconium 3-sulfopropyl phosphonate as prepared in Example 1.

Figure 9:
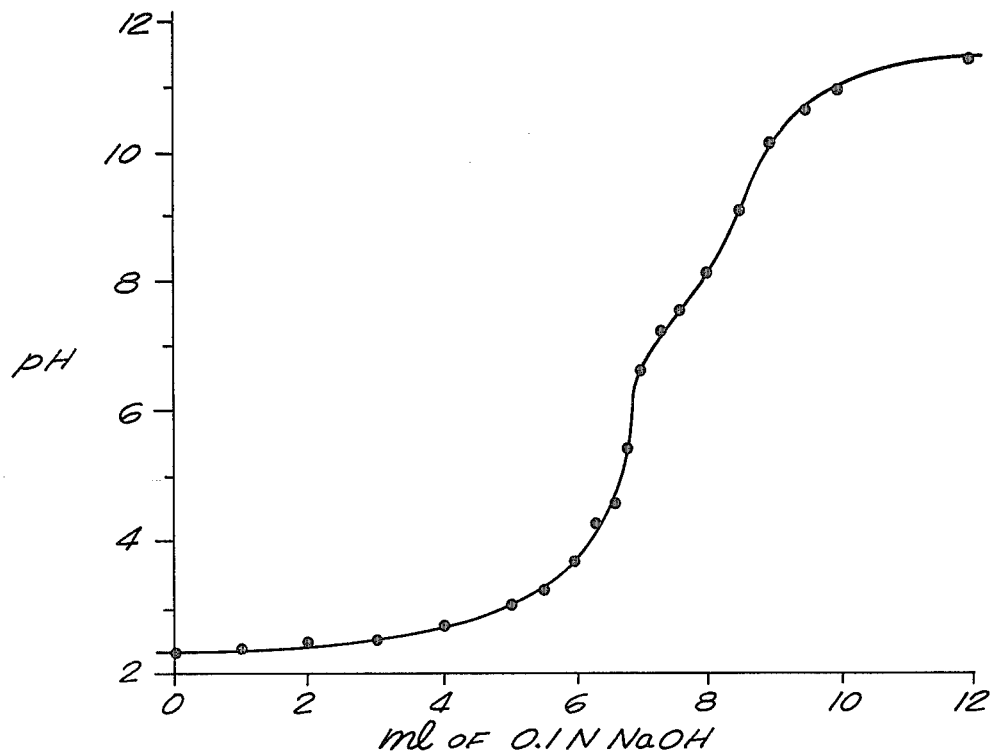

FIG. 9 is the titration curve obtained from the experiment of Example 5.

Figure 10:
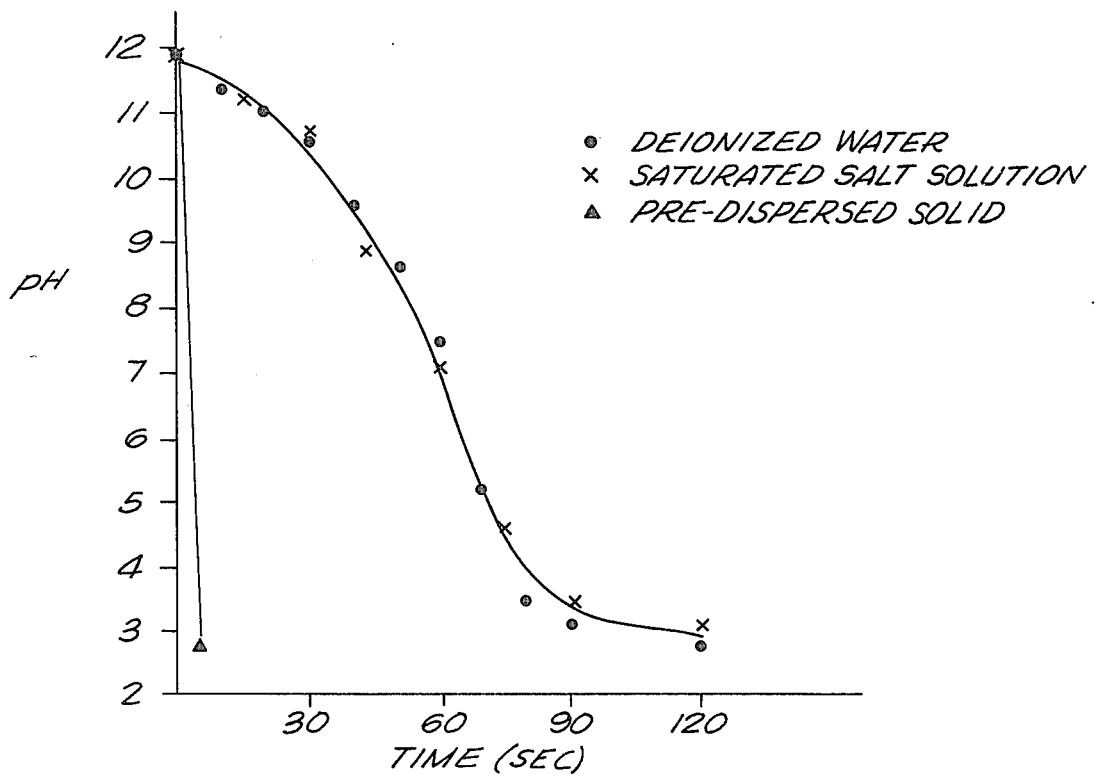

FIG. 10 is a graph showing the reaction rates from the experiments of Example 6.

DETAILED DESCRIPTION

According to the present invention, there is provided crystalline to amorphous inorganic polymers formed of structural units of the formula:

$$(O_3P-R-SO_3H)^{-2}$$

wherein R is an organo group covalently bonding the $SO_3H$ group to phosphorus and wherein each phosphorus is linked through oxygen to a tetravalent metal selected from the group consisting of zirconium, cerium, thorium, uranium, lead, titanium, hafnium, and mixtures thereof and wherein the molar ratio of phosphorus to tetravalent metal in said inorganic polymer is about 2 to 1.

Homopolymers are where inorganic phosphonate polymers have the empirical formula:

$$M(O_3PRSO_3H)_2$$

wherein R is as defined as above, with R linked to phosphorus by carbon, and M is a tetravalent metal ion selected from the group consisting of zirconium, cerium, thorium, uranium, lead, titanium, hafnium and mixtures thereof. Typically, R contains from 1 to about 17 carbon atoms, preferably from 1 to 8 carbon atoms.

The polymers are prepared by a liquid phase metathesis reaction of at least one sulfophosphonic acid compound having the formula:

$$(HO)_2OPRSO_3H$$

wherein R is as defined above, with at least one tetravalent metal ion selected from the group consisting of zirconium, thorium, cerium, uranium, hafnium, lead, titanium and mixtures thereof to form a solid inorganic polymer precipitate in which phosphorus is linked to the metal by oxygen and the sulfonate organo group is covalently bonded to the phosphorus atoms. The sulfonate group is pendent from the inorganic polymer. Typically, the tetravalent metal ion is provided as a soluble salt MX wherein M is tetravalent metal as defined above and X is the anion(s) of the salt. Typical anions include halides such as $Cl^-$, $HSO_4^{-1}$, $SO_4^{-2}$, $O_2C-CH_3^{-1}$, $NO_3^{-1}$, $O^{-2}$ and the like.

The polymeric reaction products formed have been found to be layered crystalline or semi-crystalline in nature and, as such, provide layered structures similar to zirconium phosphate. The amorphous portion of polymers possesses a large quantity of available pendent groups and is similar to silica gel.

By the term "sulfophosphorus acid compound," as used herein, there is meant a compound of the formula:

$$(HO)_2OPRSO_3H$$

wherein $RSO_3H$, is any organo group which will replace a hydroxyl of phosphoric acid and/or the hydrogen of phosphorous acid and couple to the acid by a covalent bond. Coupling to the acid may be through carbon, oxygen, silicon, sulfur, nitrogen and the like. Coupling through carbon or an oxygen-carbon group is preferred with coupling through carbon particularly preferred.

By the term "organophosphorus acid compound" as used herein, there is meant compounds, other than sulfonate terminated compounds, of the formula:

$$[(HO)_2OP]_xR'$$

wherein x is 1 or 2 and R' is an organo group other than one providing the sulfonate. Coupling is preferably through carbon or an oxygen-carbon group and may be used as indicated below as co-reactants or as exchange reactants.

When coupling is through carbon, the sulfophosphorus acid compound or the organosphosphorus acid compound is a sulfo or organo phosphonic acid and the product is a phosphonate. When coupling is through oxygen-carbon, the sulfophosphorus acid compound or organophosphorus acid compound is a sulfo or organo phosphoric monoester acid and the product a phosphate.

The general reaction for phosphonic acids alone is shown in equation (1) below and for monoesters of phosphoric acid alone by equation (2).

$$M^{+4} + 2(HO)_2PRSO_3H \rightarrow M(O_3PRSO_3H)_2 \quad (1)$$

$$M^{+4} + 2(HO)_2P(OR'')SO_3H \rightarrow M(O_3P(OR'')SO_3H)_2 \quad (2)$$

wherein R'' is the remainder of the organo group "R".

The product contains phosphorus to metal in a molar ratio of about 2 to 1, and the empirical formula for the product would show all groups bound to phosphorus.

In general, the choice of R will affect compound stability, the acidity of the sulfonate group, the hydrophilic/hydrophobic nature of the solid, interlamellar spacing, crystal size, etc.

While nowise limiting, the R groups attachable may be saturated or unsaturated, substituted and unsubstituted and include, among others, alkyl, alkylene, alkyne, aryl, alkylaryl and the like or can be partially or wholly halogen substituted, e.g., perfluoroalkyl. Typically, the group will contain from about 1 to about 17 carbon atoms, preferably from 1 to about 8 carbon atoms.

While nowise limiting, the R' groups attachable to organophosphorus acid compounds may be saturated and unsaturated, substituted and unsubstituted and include among others, alkylene, alkyloxy, alkyne, aryl, haloalky, alkylaryl, aryloxy, mercaptoalkyl, aminoalkyl, morpholinoalkyl, sulfoalkyl, phenoxyalky, betadiketo alkyl, alkyl, cyanoalkyl, cyanoalkoxy, and the like or can be partially or wholly halogen substituted.

In general, the organo group should occupy an average area of no more than about 25 $A^2$ for proper spacing. A combination of larger and smaller groups may be employed when mixed reagents are used.

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the sulfo and organophosphorus acid compounds are hygroscopic, an organic solvent such as ethanol may be employed, where water interferes with the reaction or where solubility is to be promoted. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the sulfophosphorus acid compound may serve as a solvent. Typically, the liquid medium is the liquid medium in which the sulfophosphorus acid compound is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reaction and provide an inorganic polymer diluted in respect to the sulfonate groups in proportion to the amount of phosphorous or phosphoric acid employed.

Reaction is virtually instantaneous at all temperatures leading to precipitation of layered crystalline and semicrystalline inorganic polymer solids.

An amorphous phase may appear as a gel similar to silica gel. The gel can be crystallized by extended reflux in the reaction medium, usually from about 5 to 15 hours. The semi-crystalline product is characterized by a rather broad X-ray powder pattern.

The presence of sequestering agents for the metal ion slows down the reaction and also leads to more highly crystalline products. For instance, hydrogen fluoride is a sequestering agent for zirconium and nitrate ion a sequestering agent for thorium. Both slow the reaction and promote the formation of highly crystalline end products.

As compared to zirconium phosphate forming crystals of 1–5 microns, crystals of 100 to 1000 microns in size have been prepared.

The process of preparation permits a wide variety of inorganic polymers to be formed having the characteristics of the organo group protected by the inorganic polymer structure and with subsequent exchange or substitution reactions, the formation of other inorganic polymers. Polymers formed may be block, random and the like.

For instance, a mixture of sulfo phosphorus acid compounds, mixtures of sulfo and organophosphorus acids and organo phosphorus acid compounds may be reacted with one or more of the tetravalent metal ions. If phosphorous and/or phosphoric acid is present, it will enter into the reaction as a reaction diluent.

Ion exchange activity was established for the pendant sulfonic acid groups. Prepared zirconium 3-sulfopropylphosphonate was contacted with an aqueous cupric sulfate solution, resulting in a rapid decrease in solution pH, a marked lowering of the intensity of the blue color in the solution, and a color change in the solid from white to blue.

Utility has also been established for the compounds in acid catalysis of esterification and alcohol dehydration reactions. In one experiment, a mixture of acetic acid, ethanol and zirconium 3-sulfopropylphosphonate was heated in a distillation apparatus and ethyl acetate collected as the distillate. In another experiment, a slurry of cyclohexanol and zirconium 3-sulfopropyl phosphonate was heated and a distillate of cyclohexene was collected.

The high surface area of the crystalline products also makes them useful for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from laboratory chemical suppliers. The products formed are insoluble in normal solvents and do not sublime. However, the combined weight of yield data, spectroscopy and powder diffraction results confirm the compositions reported with good reliability.

X-ray powder patterns were run on a Phillips diffractometer using CuK radiation.

Titrations were carried out in aqueous medium. A standard combination electrode and an Orion Ionalyzer pH meter were used for pH determination. The titration of the solid interlamellar anchored materials is analogous to the titration of an ion exchange resin.

EXAMPLE 1

To a one liter, three-necked flask fitted with a stirrer, addition funnel, reflux condenser and thermometer was charged 225 ml of dry toluene. A 17.2 g portion of 57% by weight sodium hydride dispersion (in mineral oil) was added with stirring.

Diethylphosphite (56.5 g) was placed in the addition funnel and added dropwise, over about two hours, to the toluene slurry. A smooth evolution of hydrogen began immediately. The addition rate was periodically adjusted to control the foam level in the reactor. Slurry temperature was between 30°–40° C. during the addition.

After addition of all the diethylphosphite, a solution of 52 g 1,3-propane sulfone in 20 ml of toluene was placed in the addition funnel, and added to the reaction mixture at a rate of about 1 ml per minute. During this addition, the temperature of the reaction mixture rose to about 60° C. The mixture was cooled to room temperature while standing overnight.

Two phases were present in the reaction mixture. The upper clear toluene phase was decanted off and the lower viscous product phase washed with two 100 ml portions of diethyl ether. The product, which had a pasty character, was placed in a glass Soxhlet extraction apparatus and continuously extracted with diethyl ether for about 40 cycles over about 6 hours.

The product, diethyl-3-sulfopropylphosphonate, sodium salt, was dried under vacuum and weighed 73 g, a yield of 63% of the theoretical weight. This product is a hygroscopic solid.

A 7.7 g portion of diethyl-3-sulfopropylphosphonate, sodium salt, was placed in a 250 ml round bottom flask fitted with a reflux condenser and a Dean-Stark trap. To this was added 30 ml of 48% by weight hydrobromic acid and the solution was refluxed. Ethyl bromide was removed in the trap, and the desired hydrolysis product, 3-sulfopropylphosphonic acid, remained in the aqueous solution and was transferred to a 250 ml three-necked flask fitted with an addition funnel.

A solution of 3.3 g $ZrOCl_2.8H_2O$ in 10 ml of water and 0.94 g of 48% by weight hydrofluoric acid was placed in the addition funnel and added dropwise to the phosphonic acid solution while the temperature was increased to boiling. A white precipitate formed very rapidly. The mixture was heated to a gentle reflux under a slow purge of nitrogen and maintained overnight.

After cooling to room temperature, the product was isolated by filtration and washed with four 25 ml portions of acetone and two 25 ml volumes of diethyl ether. The yield after oven drying at 100° C. was 4.3 g.

This highly crystalline product material, zirconium 3-sulfopropylphosphonate, had an X-ray powder diffraction pattern as shown in FIG. 8, with an interlayer spacing of 17.3 Å.

EXAMPLE 2

The procedure of Example 1 was repeated, except that no hydrofluoric acid was used and there was no nitrogen purge.

A semi-crystalline product was obtained, which had the X-ray diffraction pattern shown in FIG. 7.

EXAMPLE 3

To a 100 ml three-necked flask fitted with a stirrer, reflux condenser, Dean-Stark trap and thermometer was charged 9.6 g of 2-bromoethylsulfonic acid, sodium salt and 38 ml of triethylphosphite. The mixture was refluxed for about nine hours at a maximum temperature of 180° C., and the volatile components then removed by distillation. The residue, crude diethyl-2-sulfoethylphosphonate, sodium salt was dissolved in 18 ml of 48% by weight hydrobromic acid and refluxed for four hours to hydrolyze into 2-sulfoethylphosphonic acid.

A solution of 7.4 g $ZrOCl_2.8h_2O$ in 25 ml of water was added and the mixture refluxed for 1.5 hours. After cooling overnight at room temperature, the white solid product was isolated by filtration, washed with acetone and dried. The yield was 2.45 g of semi-crystalline zirconium 2-sulfoethylphosphonate.

EXAMPLE 4

To a 250 ml round bottom flask, fitted with a reflux condenser, magnetic stirrer and thermometer, was added 18.5 g of phenethyl bromide, 1.0 g of dichlorobutane and 25 ml of hexane. While stirring the solution, 14.2 ml of concentrated sulfuric acid was added. This mixture was heated and refluxed for about three hours.

After cooling, the lower (aqueous) phase was separated and added to ethanolic sodium hydroxide (20 g sodium hydroxide in 200 ml ethanol) with vigorous stirring. The resulting solid was separated by filtration and washed with 150 ml and 75 ml portions of ethanol.

The ethanol washings were combined, concentrated by evaporation to about 80 ml, and cooled to 0° C. A solid white product, 2-(sulfophenyl) ethyl bromide, sodium salt, was recovered by filtration, and weighed 9.70 g. The infrared spectrum showed the presence of a strong band at 1185 cm$^{-1}$ due to the —SO$_3$Na group.

A three neck 100 ml flask was arranged for product distillation and fitted with a stirrer and thermometer, then charged with 7.18 g of 2-(sulfophenyl) ethyl bromide, sodium salt, 16.6 g of triethylphosphite and 3.0 g of dimethylformamide. This mixture was stirred and heated to 120°–130° C. and ethyl bromide slowly distilled out. After maintaining the temperature for about two hours, the pasty mixture was cooled to room temperature and extracted twice with 75 ml portions of ethyl ether. The solid product was a mixture of diethyl 2-(sulfophenyl) ethylphosphonate, sodium salt and 2-(sulfophenyl) ethyl bromide, sodium salt.

To a three necked 100 ml round bottom flask fitted with a reflux condenser, Dean-Stark trap, magnetic stirrer and nitrogen purge line was added a portion of the solid containing the above-prepared phosphonate and 20 ml of 48% by weight hydrobromic acid. The mixture was refluxed until the evolution of ethyl bromide into the trap ceased. From the amount of ethyl bromide recovered, the initial weight of diethyl 2-(sulfophenyl) ethylphosphonate, sodium salt was calculated as 1.1 g.

The resulting aqueous solution, containing 2-(sulfophenyl) ethylphosphonic acid, was treated with 0.28 g of $ZrOCl_2.8H_2O$ and 0.20 g of 48% by weight hydrofluoric acid. A precipitate formed and the slurry was refluxed under a nitrogen purge for about four hours. After cooling to room temperature, the white solid product, zirconium 2-(sulfophenyl) ethylphosphonate, was separated by filtration and washing with three 50 ml portions of acetone and two 25 ml portions of ethyl ether. The product was dried under a vacuum, yielding 0.58 g. The acid titer of this material was 2.94 meq/g.

EXAMPLE 5

A 0.25 g portion of the highly crystalline product from Example 1 was dispersed in 75 ml of deionized water in a beaker and its acid equivalence determined by titration with 0.10 N sodium hydroxide solution. The data obtained are presented as FIG. 9.

The equivalence point is at 6.50 ml, corresponding to an acid content of 2.60 meq/g.

Some distortion is noted in the titration curve, after about pH 7 is reached, indicating hydrolysis reactions within the crystal in alkaline solution. This hydrolysis is not particularly rapid, as shown by pH data taken after the titration curve was obtained, as a function of time:

| Time (minutes) | pH |
|---|---|
| 0 | 11.60 |
| 6 | 11.35 |
| 15 | 11.10 |
| 21 | 10.80 |
| 55 | 9.20 |

The theoretical acid equivalence of this compound is 4.04 meq/g, a discrepancy of about 36% from the experimental value obtained. This indicates a large degree of hydration in the crystal.

EXAMPLE 6

Three experiments were performed to determine reaction rates for the sulfonic acid groups of the crystals, with the results shown in FIG. 10.

The deionized water curve was obtained by adding a 236 mg portion of a zirconium 3-sulfopropylphosphonate, prepared in a manner similar to Example 1, to a stirred solution of 10 meq sodium hydroxide in 50 ml of deionized water. The pH was monitored as a function of time and the data plotted.

A similar experiment was performed by adding 0.25 g of the compound of Example 1 to a stirred solution containing 5.00 ml of 0.10 N sodium hydroxide in 80 ml of saturated sodium chloride, and monitoring the pH as a function of time.

The predispersed solid curve was obtained by mixing 0.25 g of the product of Example 1 in 50 ml of deionized water and adding the slurry to 5 ml of 0.1 N sodium hydroxide in 50 ml of deionized water. The pH changed from 11.85 to 2.8 in less than five seconds.

EXAMPLE 7

The product of Example 1 was used as a catalyst in an esterification reaction. A 0.503 g portion was added to a distillation flask containing 2.85 ml of acetic acid and 2.85 ml of denatured ethenol. The mixture was heated and a distillate product collected. This product was identified by gas chromatography and infrared spectrophotometry as ethyl acetate.

The solid phase of the reaction mixture was recovered and weighed 0.51 g. Its X-ray diffraction pattern matched that of the initial material added.

EXAMPLE 8

A slurry of 0.100 g of the product from Example 1 and 1.0 g cyclohexanol was heated to 125° C. in a micro distillation apparatus. An essentially quantitative yield of cyclohexene was recovered in the distillate receiver, indicating utility of the zirconium 3-sulfopropylphosphonate as a catalyst for dehydrating alcohols.

EXAMPLE 9

The ion exchange capability of the product in Example 2 was demonstrated for both the sulfonic acid and sodium sulfonate forms of that compound.

A 0.50 g portion of the acid form was slurried with 10 ml of 0.215 N copper sulfate solution. The pH of the solution was initially 3.80 but immediately dropped to 0.92, the initially white solid became a pale blue color, and the blue solution color decreased markedly in intensity. Atomic absorption analysis of the solution after exchange indicated a copper concentration of 0.093 N, for copper loading in the solid of 2.46 meq/g, or 77% of the theoretical capacity.

The exchange experiment was repeated with the sodium sulfonate form of the compound. After exchange, the solution had a pH of 2.88 and a copper content of 0.135 N. Loading of the solid was calculated as 1.62 meq/g, or 51% of the theoretical capacity.

What is claimed is:

1. Inorganic phosphorus containing polymers providing pendant sulfonic acid groups, and which include units of the formula:

$$M(O_3P-R-SO_3H)_2$$

wherein R is an organo group and oxygen atoms are bonded to phosphorus and structurally linked to a tetravalent metal selected from the group consisting of zirconium, cerium, thorium, uranium, hafnium, lead, titanium and mixtures thereof and wherein the molar ratio of phosphorus to tetravalent metal in said inorganic phosphorus containing polymer is about 2 to 1.

2. Inorganic phosphorus containing polymers as in claim 1 in which R contains from 1 to about 17 carbon atoms.

3. Inorganic phosphorus containing polymers as in claim 1 in which R contains from 1 to about 8 carbon atoms.

4. Inorganic phosphonate polymers having the empirical formula $$M(O_3PRSO_3H)_2$$

wherein R is an organo group which bonds to phosphorus through carbon and M is a tetravalent metal ion selected from the group consisting of zirconium, cerium, thorium, titanium, uranium, hafnium, and lead.

5. Inorganic phosphonate polymers as in claim 4 in which R contains from 1 to about 17 carbon atoms.

6. Inorganic phosphonate polymers as in claim 4 in which R contains from 1 to about 8 carbon atoms.

7. Inorganic polymers of zirconium 3-sulfopropylphosphonate.

8. Inorganic polymers of zirconium 2-sulfoethylphosphonate.

9. Inorganic polymers of zirconium 2-(sulfophenyl) ethylphosphonate.

* * * * *

UNITED STATES PATENT AND TRADEMARK OFFICE
CERTIFICATE OF CORRECTION

PATENT NO. : 4,235,991
DATED : November 25, 1980
INVENTOR(S) : Peter M. DiGiacomo and Martin B. Dines It is certified that error appears in the above—identified patent and that said Letters Patent is hereby corrected as shown below:

Column 1, line 41, change "honogeneous" to -- homogeneous --.
Column 2, line 1, change "covalant" to -- covalent --.
Column 2, line 46, change "A" to -- An --.
Column 3, line 27, change "7.5 A" to -- 7.5 Å --.
Column 3, line 27, change "15 A" to -- 15 Å --.
Column 3, line 36, change "zorconium" to -- zirconium --.
Column 6, line 63, change "25 A$^2$" to -- 25 Å$^2$ --.
Column 7, line 53, change "organo phosphorus" to -- organophosphorus --.
Column 9, line 22, change "a" to -- A --.
Column 9, line 32, change "17.3 A" to -- 17.3 Å --.
Column 9, line 53, change "$ZrOCl_2 \cdot 8h_2O$" to -- $ZrOCl_2 \cdot 8H_2O$ --.

Signed and Sealed this

Seventh Day of April 1981

[SEAL]

Attest:

RENE D. TEGTMEYER

Attesting Officer        Acting Commissioner of Patents and Trademarks